United States Patent [19]

Nakamura et al.

[11] Patent Number: 4,477,577

[45] Date of Patent: Oct. 16, 1984

[54] NON-CONTAMINATING DIRECT SERUM ASSAY OF STEROID HORMONES

[75] Inventors: Robert M. Nakamura, Rolling Hills Estates; Daniel R. Mishell, Palos Verdes Estates, both of Calif.; Paul G. Stumpf, Palmyra, Pa.

[73] Assignee: University of Southern California, Los Angeles, Calif.

[21] Appl. No.: 303,440

[22] Filed: Sep. 18, 1981

Related U.S. Application Data

[63] Continuation-in-part of Ser. No. 130,663, Mar. 17, 1980, abandoned.

[51] Int. Cl.³ .................. G01N 33/56; G01N 33/58
[52] U.S. Cl. .................. 436/510; 436/536; 436/542; 436/826; 436/817; 436/825
[58] Field of Search .................. 424/1; 436/510, 536, 436/542, 826, 817, 825

[56] References Cited

U.S. PATENT DOCUMENTS

| | | | |
|---|---|---|---|
| 4,208,400 | 6/1980 | Edwards | 424/1 |
| 4,225,574 | 9/1980 | Romelli et al. | 424/1 |
| 4,311,690 | 1/1982 | Buehler et al. | 424/1 |
| 4,366,143 | 12/1982 | Midgley et al. | 424/1 |

*Primary Examiner*—Christine M. Nucker
*Attorney, Agent, or Firm*—Nilsson, Robbins, Dalgarn, Berliner, Carson & Wurst

[57] ABSTRACT

A method for direct serum assay of steroid hormones wherein the competition from binding protein, having an affinity for complexing with the steroid hormones, is significantly eliminated by adding to the serum an artificial compound which has a greater or equal affinity for the binding protein than do the steroid hormones, and which is not immuno-reactive with the steroid hormones. Because the compound is artificial, it is non-contaminating. Levonorgestrel and norethindrone as such compounds are disclosed.

10 Claims, 1 Drawing Figure

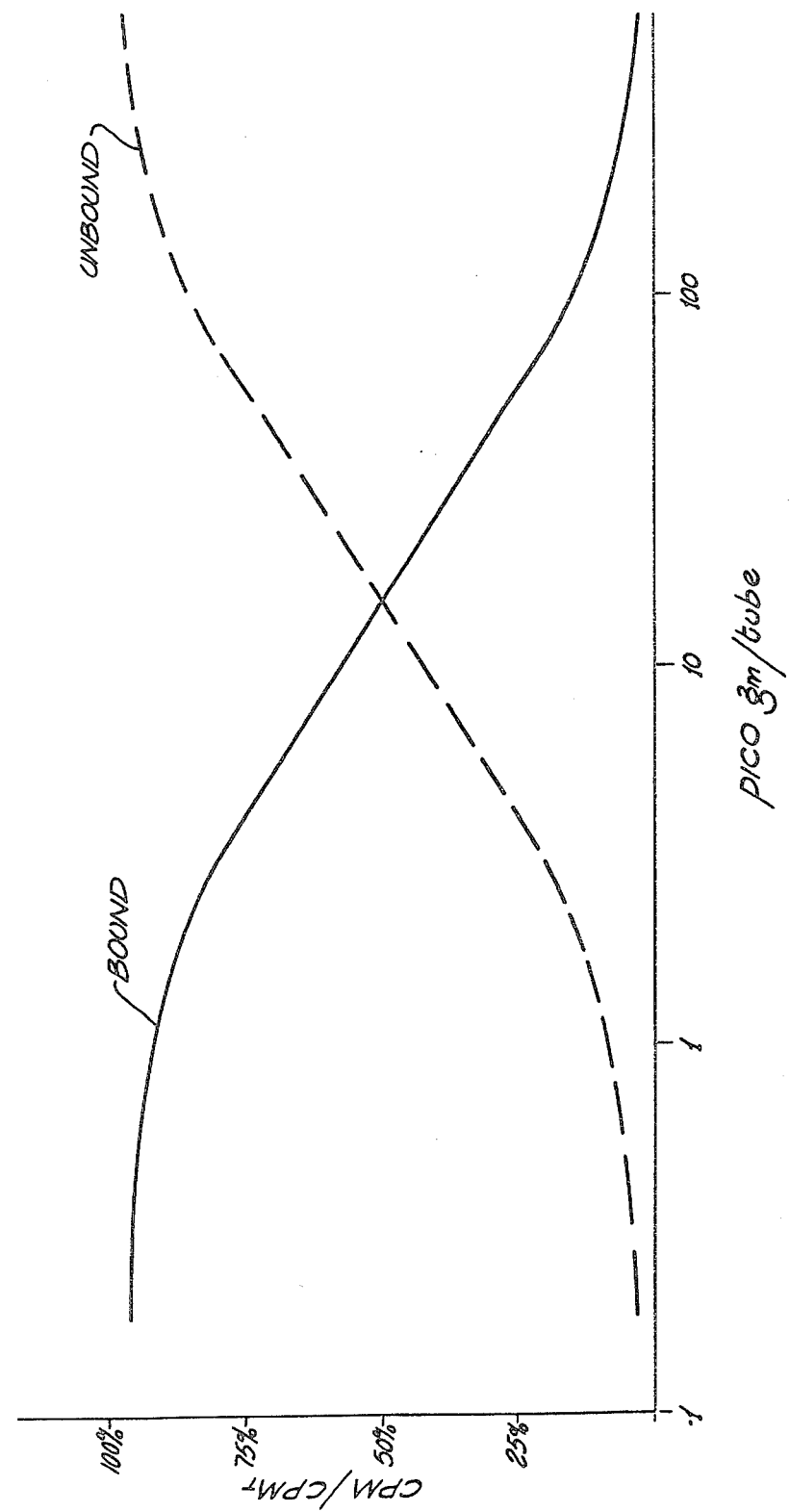

NON-CONTAMINATING DIRECT SERUM ASSAY OF STEROID HORMONES

CROSS REFERENCE TO RELATED APPLICATION

This application is a continuation-in-part of application Ser. No. 130,663, filed Mar. 17, 1980, now abandoned, entitled Direct Serum Assay of Steroid Hormones.

BACKGROUND OF THE INVENTION

This invention relates generally to a novel method of direct serum assay of steroid hormones of the type conducted without the need to extract the hormones from the serum prior to assay. More particularly, this invention concerns reducing or eliminating the binding protein competition from interacting with steroid hormones prior to the stage in the assay when the bound or unbound antigen (tagged and untagged) is separated for counting, by adding an artificial compound having a greater or equal affinity for the binding protein than do the steroid hormones, and which is non-immuno-reactive with the steroid hormones. Because the compound is artificial, it is non-contaminating.

In the past, it has been common practice to assay for a selected antigen, e.g., one of the steroid hormones, by employing a model antigen and an antibody which is specific to the antigen it is desired to assay, which model antigen is tagged in some way, e.g. with a radionuclide or an enzyme. In such an assay, e.g., a radioimmuno-assay, a radioactively tagged antigen, and the specific antibody are added to the serum. The added antibody is made specific by, e.g., in the case of the human steroid hormone estradiol, estradiol coupled to a protein may be added in vivo to an animal, e.g., a rabbit. The rabbit's system will produce an antibody to the estradiol. The model, i.e., tagged, antigen is added in a quantity sufficient to exceed the number of binding sites available in the amount of added antibody. Typically, the tagged antigen will be added to exceed the antibody by at least a factor of two. Thus, typically, after addition, the serum will contain:

where the * indicates the model or tagged antigen is modified in some way, as by tagging with a radionuclide or an enzyme, which will enable quantitation in the assay.

Once the tagged antigen complexes with the available specific antibody the serum will contain:

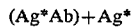

which is typically referred to as bound [(Ag*Ab)] and unbound [Ag*]. To conduct the assay it then is only necessary to separate the bound from the unbound fractions and compare the amount of radioactivity (or other tagging mechanism), in either of the separated portions of the serum containing the bound or the unbound fraction, with the total amount of radioactivity (or other tagging mechanism) initially added, then by use of a standard curve as is shown in FIG. 1 the amount of the untagged hormone or antigen which it is desired to assay can be determined.

The curve shown as a solid line in FIG. 1 is the standard curve for determining the amount of target antigen present in a sample being assayed by counting the amount of tagged antigen bound to the specific antibody. As can be seen, the larger the amount of tagged bound antigen in the bound fraction, which includes both tagged (model) and untagged (target) antigen bound to the specific antibody (in the case of a radioactive tagging illustrated in FIG. 1), the higher the percentage counts per minutes, compared to the total counts per minute of the added tagged antigen, and the lower the concentration of the target hormone being assayed. This is due to the fact that both the added antibody which is necessary to bind the antigen (tagged or untagged) in a given sample of serum and the amount of tagged antigen added are constants. The standard curve is developed by decreasing the ratio of the tagged to the untagged antigen, specific to the antibody in standardized sample runs with known amounts of untagged antigen. In the assay itself, tagged antigen and antibody are added to the serum which already contains the natural target antigen. Because both tagged and untagged antigen compete for sites on the antibody (which is in a known constant amount and specific to the added tagged antigen and untagged antigen present in the serum sample) to complex with that antibody, a higher amount of tagged antigen measured in the separated bound Ag*Ab complex indicates a smaller concentration of untagged antigen for which the assay is conducted.

Correspondingly, the percentage of the tagged antigen remaining in the separated unbound portion of the serum increases as the amount of available untagged antigen, for which the assay is being conducted, increases in the serum sample.

As is well known in the art, the bound fraction can be separated from the unbound by adding to the serum a further antibody from a different species which is specific to the antibody so that the antigen antibody complex (tagged and untagged), i.e., the bound antigens, in the serum and the resultant double antibody complex will precipitate out, leaving the unbound tagged and untagged antigen in the supernatant of the serum sample. For example, if the antibody, an immunoglobulin, is produced in rabbits, the rabbit serum selected to be specific to the antigen to be assayed, an antibody from, e.g., a donkey serum, specific to the rabbit immunoglobulin will complex with the rabbit Ag*Ab tagged complex and the untagged AbAg complex in the serum of the assay. The sheer size of this new complex will cause it to precipitate out of the serum leaving the unbound Ag* and the unbound untagged Ag in the supernatant of the serum.

Also, as is well known in the art, the unbound Ag* and untagged Ag can be separated by adding a fine charcoal suspension which will absorb the Ag* and untagged Ag by surface adhesion to the charcoal. Centrifuging will then separate the absorbed unbound Ag* and untagged Ag from the serum leaving the bound Ag*Ab complex and the bound untagged AgAb complex in the supernatant.

The problem known in the art in assaying sex steroid hormones from, e.g., human serum samples, is that the sex steroid hormones occur in such minute quantities. Such quantities are typically on the order of from about 5 to about 700 picogram/ml for, e.g., estrogens, depending on the age and other biological factors pertaining to the patient from whom the serum is drawn and the hormone cannot be quantitively extracted with organic solvents. This results in the rigid requirement that the amount of hormone extracted by the state of the art methods be known, resulting in extra steps to ensure that the results are accurate. Presently known methods utilize the addition of a very minute known amount of tagged antigen (as a tracer) to the serum prior to extraction followed by counting the extract to determine the percent of antigen extracted. For direct serum assay, the low recovery results in the placing of the bound and unbound fractions on the flat portions of the standard curve shown in FIG. 1. Thus, the ability to determine the amount of the sex steroid hormone in a direct assay in the serum, based upon either a variation in the amount of tagged antigen remaining in the unbound fraction or in the amount of tagged antigen complexing into the bound fraction, is not readily possible. What is possible in the prior art methods is to measure the apparent rather than the actual amount of steroid hormone by shifting the standard curve. However, since the amount of steroid hormone unbound by SHBG in any given patient varies at any given time from approximately 2% to approximately 30%, callibration of the shifted standard curve is not possible. The problem of being on the flat portion of the standard curve could be circumvented by extracting about an order of magnitude larger quantity of serum (i.e., blood) from the patient, to increase the available quantities of steroid hormone sufficiently to shift the standard curve, but when numerous hormones are to be tested from one patient, this becomes an impractical amount of serum extraction. However, apparent and not actual steroid hormone content is being measured due to the inability to know the percent bound by the binding protein.

The factor which accounts for this set of requirements is the presence in the serum of the binding protein, referred to in the art as either SHBG or SSBG or TeBG, and also as simply BP. SHBG has a great affinity for the steroid hormones which will compete with the antibody. This binding protein is also responsible for the incomplete extraction. In human serum, the, e.g., sex steroid hormones exist in the free, i.e., unbound to SHBG, state in typically from 2-30% of the total available sex steroid hormone. Since the binding protein has about the same affinity for sex steroid hormones as the antibody, little displacement of the bound sex steroid hormones to the antibody from the binding protein occurs when the antibody is added to the serum. Therefore, typically only about 2-30% of the sex steroid hormone, i.e., that amount unbound to the binding protein in the sample serum, is available for competing with the added tagged antigen to complex with the added antibody. This is the basis for the decrease of the available sex steroid hormone for competing with the added tagged, e.g., with radio-nuclide, antigen, hindering the direct radioimmunoassay of sex steroid hormones.

Thus for example, with estradiol in human serum

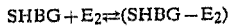

$$SHBG + E_2 \rightleftharpoons (SHBG - E_2)$$

The association constant for this $SHBG - E_2$ complex is $10^9$ liters/moles with the corresponding dissociation constant being $10^{-9}$ (liters/moles$^{-1}$). The dissociation constant for the free antibody is approximately $3 \times 10^{-10}$ (liters/moles$^{-1}$). So long as this is within an order of magnitude of that for SHBG, the SHBG will very effectively compete with the added tagged antigen for sites to complex with estradiol.

In the past it has been known to extract the steroid hormones in the serum sample by using an appropriate organic solvent. This process takes time and several steps to complete, since extraction of the hormone is incomplete, both of which make such a procedure unattractive to a commercial laboratory in the business of analyzing serum samples for the presence of, among other things, steroid hormones.

It has also been known to add dihydrotestosterone (DHT) to free more of the, e.g., sex steroid hormones from the binding protein due to the greater affinity of SHBG for DHT than for the other sex steroid hormones. This addition of DHT places a greater amount of the other sex steroid hormones in the free state in the serum. Assay then can be accomplished of this greater amount of other free sex steroid hormones. A problem which occurs in using this technique is that DHT also occurs in sample serums in amounts comparable to the other sex steroid hormones and is often desired to be measured. Using DHT in the commercial laboratory setting to free the sex steroid hormones from the binding protein for assay thereof, creates the significant potential for contaminating the laboratory, its technicians or equipment, with DHT, thus interfering with other measurements being conducted of DHT. Because DHT occurs in such small quantities in serum samples it would have to be added in such relatively large quantities to displace the, e.g., sex steroid hormones from the SHBG, the potential for significant DHT contamination of the laboratory exists. It is further known in the art as disclosed by Green, Marshall, Pensky and Stanbury, "Thyroxin Binding Globulin: Characterization of the Binding Site with a Fluorescent Die as a Probe," *Science*, Vol. 175, at 1378 (1972), that ANS (8-anolino 1-naphthalenesulfonic acid) can be used to displace the thyroid hormone from thyroxine binding protein (TBG—thyroxine binding globulin) for direct assay purposes. ANS is an allostere of thyroid hormone for TBG. Also known, as described in Edward U.S. Pat. No. 4,208,400, is the incorporation of progesterone in an incubated assay mixture containing unconjugated oestriol. Here too, a significant potential for contamination exists, interfering with other assays, for example, the assay of progesterone itself.

While such prior art methods have exhibited at best a degree of utility, room for significant improvement in the methods of assay of steroid hormones of the prior art remains. The need clearly exists for a direct serum assay of steroid hormones without the need to add DHT to the serum and which can be conducted without the fear of contamination of other test procedures.

The problems enumerated in the foregoing are not intended to be exhaustive, but rather are among many which tend to impair the effectiveness of previously known methods of assay of steroid hormones. Other noteworthy problems may also exist; however, those presented above should be sufficient to demonstrate that methods of assay of steroid hormones appearing in the prior art have not been altogether satisfactory.

SUMMARY OF THE INVENTION

Recognizing the need for an improved method of assay of steroid hormones, it is a general feature of the present invention to provide a novel direct steroid hormone assay which minimizes or reduces the problems of the type previously noted.

It is a more particular feature of the present invention to provide a direct serum assay of steroid hormones wherein competition from binding proteins, having an affinity for complexing with the steroid hormone, which it is desired to assay, on the same order of magnitude as the added antibody specific to the steroid hormone which it is desired to assay, is substantially eliminated by adding to the serum an artificial compound which has a greater or equal affinity for the binding protein than does the steroid hormone and which is non-immunoreactive with the steroid hormone which it is desired to assay. By artificial is meant a synthesized compound which does not exist naturally in the animal whose serum is being assayed. Examples of such artificial compounds include levonorgestrel and norethindrone.

Examples of the more important features of the present invention have thus been summarized rather broadly in order that the detailed description thereof that follows may be better understood, and in order that the contribution to the art may be better appreciated. There are, of course, additional features of the invention that will be described hereafter and which will also form the subject of the appended claims. These other features and advantages of the present invention will become more apparent with reference to the following detailed description of a preferred embodiment thereof in connection with the accompanying drawings, in which:

FIG. 1 shows a conventional standard curve for determining the amount of antigen (hormone) in a serum sample from the amount of added tagged antigen specific to an added antibody which either remains unbound or binds with the antibody.

DETAILED DESCRIPTION OF A PREFERRED EMBODIMENT

Turning now to FIG. 1, there is shown, as has been discussed above, a typical standard curve for determining the unknown amount of an untagged antigen in a serum sample of which the assay is being conducted by radioimmuno-assay, through measuring either the amount of tagged antigen remaining in the unbound fraction or the amount which complexes with the antibody which it is desired to assay.

As is well known in the art, a standard curve can be produced by having serum samples containing known different amount of untagged antigen and adding to each a known constant amount of specific antibody and a known constant amount of tagged antigen. After separation of the bound and unbound fractions from each sample the competition of the tagged and untagged antigen for the known amount of specific antibody can be determined for each known different amount of untagged antigen in the various samples. From this a standard curve is produced to compare the measured amounts of bound and unbound tagged antigen observed assaying when assaying serum samples with an unknown amount of untagged antigen.

The purpose of the present invention is to overcome the problems existing in the prior art in measuring the amount of steroid hormone antigen in a direct serum assay. These problems, as has been explained above, are due to the fact that in an assay of steroid hormones, which occur in, e.g., human serum samples, in such minute quantities, and which have a near equal affinity for SHBG as for added antibody, the assay counting falls on the flat horizontal portions of the standard curve at the low concentration (i.e., the left hand) end of the curves of FIG. 1, for both the bound and unbound fractions of the tagged antigen, due to the falsely low value determined by measuring only the unbound fraction of the hormone.

In order to eliminate the competition from the SHBG and place the assay counting on the sloped portion of the standard curve, while at the same time avoiding the problems of the prior art associated with using DHT to displace the steroid hormones to the free state in the serum, the present invention employs the addition to the serum of a compound having an effectively competing affinity for SHBG with the steroid hormone, which it is desired to assay, and which compound is an artificial compound and is non-immunoreactive with the antibody to the steroid hormone.

Such a compound is D-norgestrel (d-Ng), also known in the art as levenorgestrel, which is a synthetic gestagen derived from 19-nor-testosterone. Levenorgestrel is the World Health Organization nomenclature for the active d form of d-1 norgestrel racemate. It is added to the serum before conducting the assay, e.g., radioimmuno-assay. The synthetic hormone levenorgestrel is an isostere of DHT, being structurally, but not functionally, similar to DHT. The addition of levenorgestrel to the serum displaces the other steroid hormones from the binding protein, leaving them free to complex with the added antibody for purposes of the assay. Another such compound is norethindrone, also known as 19-norethisterone or 17-hydroxy-19-nor-17a-pregn-4-en-20-yn-3-one.

In FIG. 1, a typical standard curve is shown for the bound (solid line) and unbound (dashed line) fractions. The curve gives a measure of the counts per minute (CPM) in the separated fraction as a percentage of the total counts per minute in the tagged antigen added to the sample. Since a known amount of antibody and tagged antigen is added to a number of different standard samples of the target antigen, the standard curve correlates the percentage $CPM_S/CPM_T$ where $CPM_S$ is the counts per minute in the separated fraction (bound or unbound respectively) and $CPM_T$ is the total counts per minute of the added tagged antigen.

As can clearly be seen from FIG. 1, the percentage decreases for the bound fraction as the amount of target antigen in the standard samples increases. For the examplary curve shown in FIG. 1, the straight portion of the curve runs from about 3 picogm/tube to about 75 picogm/tube (where a tube measures 0.1 ml) with the respective percentages being 80% and 20%. For concentrations below 3 picogm/tube and above 75 picogm/tube, the curve flattens out. Similarly, for the unbound fraction, the straight portion of the curve occurs between 3 picogm/tube (at 20%) and 75 picogm/tube (at 80%), below and above which points, respectively, the curve begins to flatten out. The 50% point for each curve is at 15 picogm/tube.

Using the standard curve, an assay can be conducted of a sample containing an unknown amount of the target antigen by adding the same known constant amounts of specific antibody and model (tagged) antigen to the sample as was used to generate the standard curve, and determining the $CPM_S/CPM_T$ percentage in either the bound or unbound fraction. The appropriate curve (bound or unbound) then gives the concentration on the abcissa of the target hormone, i.e., untagged antigen.

Using the assay method according to the present invention, with levenorgestrel as the artificial compound, to assay for estradiol on four separate serum samples, which were also assayed using the prior art technique of extracting the target hormone by using an organic solvent, the concentrations in Table I in picogm/ml were found:

TABLE I

| Sample # | Extracted Assay | Direct Serum Assay |
|---|---|---|
| 1 | 92 picogm/ml | 80 picogm/ml |
| 2 | 77 picogm/ml | 69 picogm/ml |
| 3 | 79 picogm/ml | 58 picogm/ml |
| 4 | 124 picogm/ml | 109 picogm/ml |

These results were found to be both correlatable and reproducible within acceptable variances. The reason the assay values were consistently lower for the assay method according to the present invention, compared to an assay in which the estradiol was first extracted from the serum sample, is not known. However, it is believed that the results according to the assay method of the present invention are, more likely, the better representative values for the estradiol concentration in each particular sample.

Among the steroid hormones for which the assay method according to the present invention is useful are the sex steroid hormones, e.g., estrogens and androgens, and other steroid hormones, e.g., the 21 carbon steroids, e.g., corticoids and gestagens. For example, levonorgestrel has been found effective to free the sex steroid hormones from the SHBG.

SUMMARY OF ADVANTAGES AND SCOPE OF THE INVENTION

It will be appreciated that in performing a method of direct serum assay of steroid hormones according to the present invention, certain significant advantages are provided.

In particular, steroid hormones can be assayed in a non-contaminating manner without the need to extract and determine recovery of the steroid hormone from the sample serum by use of an organic solvent or without the need of adding DHT to the serum to displace the steroid hormones from the binding protein.

The foregoing description of the invention has been directed to a particular preferred embodiment in accordance with the requirements of the patent statutes and for purposes of explanation and illustration. It will be apparent, however, to those of ordinary skill in this art that many modifications and changes in the method of the present invention may be made without departing from the scope and spirit of the invention. For example, artificial compounds other than levonorgestrel and norethindrone, which possess the necessary properties, of having an effectively competing affinity for the binding protein and being non-immuno-reactive with the sex steroid hormones, can be used.

It will be further apparent that the invention may also be utilized with suitable modifications within the state of the art. Some examples of these include the use of the present method in any assay where competition from binding protein decreases the sensitivity of the assay.

These and other modifications of the invention will be apparent to those skilled in the art. It is Applicant's intention in the following claims to cover all such equivalent modifications and variations as fall within the true spirit and scope of the invention.

What is claimed is:

1. In a method for direct serum assay of a target steroid hormone, employing the counting of a tagged antigen, in which binding protein competes with an antibody that is added to the serum sample along with the tagged antigen for the target steroid hormone, the improvement comprising:
    adding to the serum a synthesized compound which does not exist naturally in the serum being assayed, said component being non-immuno-reactive with the antibody and having sufficient competing affinity for binding protein with the target steroid hormone to release an amount of the target steroid hormone sufficient to permit accurate quantification thereof.

2. The method of claim 1 wherein the target steroid hormone is a sex steroid hormone.

3. The method of claim 2 wherein the sex steroid hormone is of the group consisting of:
    estrogens; and,
    androgens.

4. The method of claim 1 wherein the target steroid hormone is a 21 carbon steroid.

5. The method of claim 2 or 4 in which the compound is levonorgestrel.

6. The method of claim 2 or 4 in which the compound is norethindrone.

7. In a method for direct serum assay of a target steroid hormone, employing the counting of a tagged antigen, in which binding protein competes with an antibody that is added to the serum sample along with the tagged antigen, for the target steroid hormone, the improvement comprising:
    adding levonorgestrel to the serum, sufficient to effectively free the untagged antigen from the binding protein.

8. The method of claim 3 wherein the compound is levonorgestral and the target steroid hormone comprises a 21 carbon steroid.

9. In a method for direct serum assay of a target steroid hormone, employing the counting of a tagged antigen, in which binding protein competes with an antibody that is added to the serum sample along with the tagged antigen, for the target steroid hormone, the improvement comprising:
    adding norethindrone to the serum, sufficient to effectively free the untagged antigen from the binding protein.

10. The method of claim 3 wherein the compound is norethindrone and the target steroid hormone comprises a 21 carbon steroid.

* * * * *